(12) United States Patent
Boeck

(10) Patent No.: US 7,870,856 B2
(45) Date of Patent: Jan. 18, 2011

(54) INHALER

(75) Inventor: Georg Boeck, Laupheim (DE)

(73) Assignee: Boehringer Ingelheim International GmbH, Ingelhiem am Rhien (DE)

( * ) Notice: Subject to any disclaimer, the term of this patent is extended or adjusted under 35 U.S.C. 154(b) by 952 days.

(21) Appl. No.: 11/733,399

(22) Filed: Apr. 10, 2007

(65) Prior Publication Data

US 2007/0240713 A1    Oct. 18, 2007

(30) Foreign Application Priority Data

Apr. 11, 2006  (DE) ................ 10 2006 016 903

(51) Int. Cl.
A61M 11/00 (2006.01)
(52) U.S. Cl. .................. 128/203.21; 128/203.15
(58) Field of Classification Search .......... 128/203.12, 128/203.15, 203.21, 203.24
See application file for complete search history.

(56) References Cited

U.S. PATENT DOCUMENTS

| | | | |
|---|---|---|---|
| 3,807,400 A | 4/1974 | Cocozza | |
| 3,921,637 A * | 11/1975 | Bennie et al. | 128/203.15 |
| 3,991,761 A | 11/1976 | Cocozza | |
| 4,069,819 A | 1/1978 | Valentini et al. | |
| 4,889,114 A | 12/1989 | Kladders | |
| 4,995,385 A | 2/1991 | Valentini et al. | |
| 5,152,284 A | 10/1992 | Valentini et al. | |
| 5,619,985 A * | 4/1997 | Ohki et al. | 128/203.21 |
| 5,673,686 A | 10/1997 | Villax et al. | |
| 5,715,811 A * | 2/1998 | Ohki et al. | 128/203.21 |
| 5,881,721 A | 3/1999 | Bunce et al. | |
| 5,947,118 A | 9/1999 | Hochrainer et al. | |
| 6,298,846 B1 * | 10/2001 | Ohki et al. | 128/203.15 |
| 6,341,605 B1 * | 1/2002 | Ohki et al. | 128/203.15 |
| 6,443,152 B1 * | 9/2002 | Lockhart et al. | 128/203.21 |
| 6,488,027 B1 | 12/2002 | Moulin | |
| 6,679,256 B2 | 1/2004 | Ingle et al. | |
| 6,705,313 B2 * | 3/2004 | Niccolai | 128/203.21 |
| 6,715,485 B1 | 4/2004 | Djupesland | |
| 7,270,127 B2 * | 9/2007 | Lockhart et al. | 128/203.15 |
| 7,708,011 B2 | 5/2010 | Hochrainer et al. | |
| 2002/0162552 A1 | 11/2002 | Pera | |
| 2005/0263151 A1 | 12/2005 | Hochrainer et al. | |
| 2007/0240713 A1 | 10/2007 | Boeck | |

(Continued)

FOREIGN PATENT DOCUMENTS

CA    2064860 A1    2/1991

(Continued)

OTHER PUBLICATIONS

Bell, J.H. et al., "Dry Powder Aerosols I: A New Powder Inhalation Device", Journal Pharmaceutical Science, 1971, vol. 60, No. 10, pp. 1559-1564.

(Continued)

Primary Examiner—Steven O Douglas
(74) Attorney, Agent, or Firm—Michael P. Morris; David L. Kershner

(57) ABSTRACT

An inhaler for administering a medicament in the form of inhalable substances, formulations or mixtures of substances comprises a housing (1) having an inner cavity for holding the medicament, which is coupled to a mouthpiece (2). The housing (1) is rigidly connected to the mouthpiece (2).

18 Claims, 1 Drawing Sheet

U.S. PATENT DOCUMENTS

| | | |
|---|---|---|
| 2009/0194105 A1 | 8/2009 | Besseler et al. |
| 2009/0235929 A1 | 9/2009 | Egen et al. |

FOREIGN PATENT DOCUMENTS

| | | |
|---|---|---|
| DE | 3345722 A1 | 6/1985 |
| EP | 129985 A1 | 1/1985 |
| EP | 0388621 A1 | 9/1990 |
| EP | 0591136 A1 | 4/1994 |
| EP | 0666085 A1 | 8/1995 |
| EP | 0869079 A2 | 10/1998 |
| EP | 1238680 A1 | 9/2002 |
| FR | 2146202 A1 | 3/1973 |
| WO | 9428958 A1 | 12/1994 |
| WO | 9945987 A1 | 9/1999 |
| WO | 0051672 A1 | 9/2000 |
| WO | 2006090149 A2 | 8/2006 |
| WO | 2007116002 A1 | 10/2007 |

OTHER PUBLICATIONS

Cox, J.S.G. et al., "Administration of Disodium Cromoglycate", Medical Journal, 1969, p634.

International Search Report for PCT/EP2007/053335 mailed Jul. 6, 2007.

* cited by examiner

INHALER

BACKGROUND OF THE INVENTION

This application claims priority of DE 10 2006 016 903, filed Apr. 11, 2006, the entirety of which is incorporated herein by reference.

FIELD OF THE INVENTION

The invention relates to an inhaler for administering a medicament in the form of inhalable substances, formulations or mixtures of substances having a housing comprising an inner cavity for holding the substances, which is coupled to a mouthpiece.

DESCRIPTION OF THE PRIOR ART

EP 0 911 047 A1 discloses an inhaler for inhaling powdered medicaments from capsules, which comprises a lower part having two windows and a plate in which are provided capsule holders and air inlet openings. In addition, an inhalation chamber is connected to the plate, on which is provided a head having two sharp pins which is movable counter to a spring. A mouthpiece tube is connected to an upper part of the inhaler and a lid is foldably connected to the lower part, the plate and the upper part.

In order to inhale the medicament effectively, the patient has to bring the mouthpiece of the inhaler into contact with the oral mucosa (lips, oral/pharyngeal cavity). This proves to be problematic inasmuch as the oral mucosa in all humans contain a variably large number of all kinds of bacteria and other micro-organisms some of which are pathogenic. Therefore the mouthpiece of the inhaler becomes contaminated when used. Patients and hence users of inhalers are advised to clean the mouthpiece after using the inhaler, but the cleaning process will consequently be carried out with different degrees of thoroughness depending on the personal habits of the patient, their age and how ill they are. Furthermore, the interior of the housing of the inhaler must also be cleaned, particularly to remove drug residues, as these residues may lead to dosage problems if they break away at irregular intervals and are delivered with the proper dose.

The problem of the invention is to provide an inhaler of the type mentioned hereinbefore which is easy for a patient to operate.

SUMMARY OF THE INVENTION

According to the invention the problem is solved by having the housing rigidly connected to the mouthpiece.

There is provided an inhaler for administering a medicament in the form of inhalable substances, formulations or mixtures of substances comprises a housing (1) having an inner cavity for holding the medicament, which is coupled to a mouthpiece (2). The housing (1) is rigidly connected to the mouthpiece (2).

BRIEF DESCRIPTION OF THE DRAWINGS

The invention will hereinafter be described in more detail using a number of embodiments by way of example, with reference to the accompanying drawings. In the drawings.

DETAILED DESCRIPTION OF THE INVENTION

Figure 1:
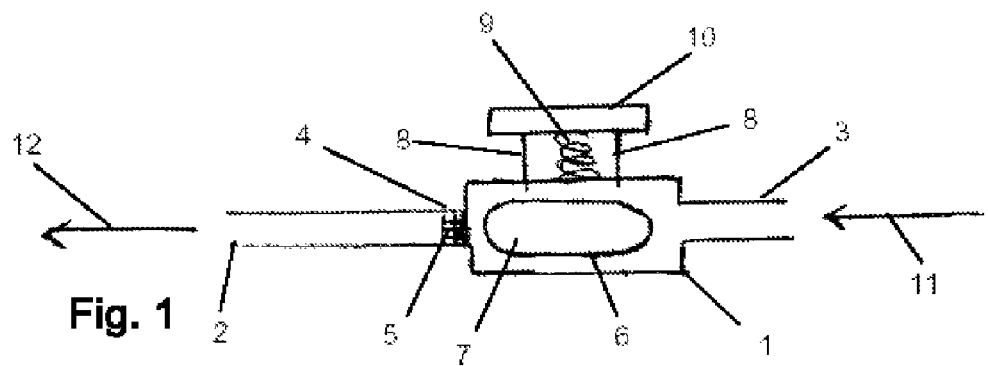
FIG. 1 is a schematic view of an inhaler according to the invention.

The housing or inner cavity of the housing is supplied with the accurately metered dose of medicament by the manufacturer and there is no need to flip the mouthpiece away from the housing in order to insert a drug-filled capsule in the housing, in the manner known in the art. Rather, the mouthpiece is rigidly connected to the housing such that a user of the inhaler cannot open up the housing to fill the inner cavity with the drug. This inhaler is advantageous in that it can be manufactured cheaply for single use from a small number of individual parts and comprises only components which are absolutely necessary, namely the housing and the mouthpiece. Its construction as a single-use inhaler also makes it easier to operate as there is no need for regular cleaning, in particular, and drug residues in the inhaler cannot affect its use. The mouthpiece can be in the form of a simple tube with no ergonomic shaping and may be clipped to the housing, for example. Moreover, there is no need for the user or patient to carry around an inhaler and, separately, the substance which is to be inhaled.

Inhalers are known under the brand names HandiHaler®, Spinhaler®, Rotahaler®, Aerolizer®, Flowcaps®, Turbospin®, AIR DPI®, Orbital®, Directhaler® and/or described in DE 33 45 722, EP 0 591 136, DE 43 18 455, WO 91/02558, FR-A-2 146 202, US-A-4 069 819, EP 666085, EP 869079, U.S. Pat. No. 3,991,761, WO 99/45987, WO 200051672, Bell, J. Pharm. Sci. 60, 1559 (1971); Cox, Brit. Med. J. 2, 634 (1969). Single- and multi-dose powder inhalers are known, particularly the Spinhaler®, Rotahaler®, Aerolizer®, Inhalator®, HandiHaler®, Diskhaler®, Diskus®, Accuhaler®, Aerohaler®, Eclipse®, Turbohaler®, Turbuhaler®, Easyhaler®, Novolizer®, Clickhaler®, Pulvinal®, Novolizer®, SkyeHaler®, Xcelovair®, Pulvina®, Taifun®, MAGhaler®, Twisthaler® and the Jethaler®.

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and P13-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and

- 3-(4-{6-[2-hydroxy-2-(4-hydroxy-3-hydroxymethyl-phenyl)-ethylamino]-hexyloxy}-butyl)-benzyl-sulphonamide
- 5-[2-(5.6-diethyl-indan-2-ylamino)-1-hydroxy-ethyl]-8-hydroxy-1H-quinolin-2-one
- 4-hydroxy-7-[2-{[2-{[3-(2-phenylethoxy)propyl]sulphonyl}ethyl]-amino}ethyl]-2(3H)-benzothiazolone
- 1-(2-fluoro-4-hydroxyphenyl)-2-[4-(1-benzimidazolyl)-2-methyl-2-butylamino]ethanol
- 1-[3-(4-methoxybenzyl-amino)-4-hydroxyphenyl]-2-[4-(1-benzimidazolyl)-2-methyl-2-butylamino]ethanol
- 1-[2H-5-hydroxy-3-oxo-4H-1,4-benzoxazin-8-yl]-2-[3-(4-N,N-dimethylaminophenyl)-2-methyl-2-propylamino]ethanol
- 1-[2H-5-hydroxy-3-oxo-4H-1,4-benzoxazin-8-yl]-2-[3-(4-methoxyphenyl)-2-methyl-2-propylamino]ethanol
- 1-[2H-5-hydroxy-3-oxo-4H-1,4-benzoxazin-8-yl]-2-[3-(4-n-butyloxyphenyl)-2-methyl-2-propylamino]ethanol
- 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
- 5-hydroxy-8-(1-hydroxy-2-isopropylaminobutyl)-2H-1,4-benzoxazin-3-(4H)-one
- 1-(4-amino-3-chloro-5-trifluoromethylphenyl)-2-tert.-butylamino)ethanol
- 6-hydroxy-8-{1-hydroxy-2-[2-(4-methoxy-phenyl)-1,1-dimethyl-ethylamino]-ethyl}-4H-benzo[1, 4]oxazin-3-one
- 6-hydroxy-8-{1-hydroxy-2-[2-(ethyl 4-phenoxy-acetate)-1,1-dimethyl-ethylamino]-ethyl}-4H-benzo[1,4]oxazin-3-one
- 6-hydroxy-8-{1-hydroxy-2-[2-(4-phenoxy-acetic acid)-1,1-dimethyl-ethylamino]-ethyl}-4H-benzo[1,4]oxazin-3-one
- 8-{2-[1,1-dimethyl-2-(2.4.6-trimethylphenyl)-ethylamino]-1-hydroxy-ethyl}-6-hydroxy-4H-benzo[1,4]oxazin-3-one
- 6-hydroxy-8-{1-hydroxy-2-[2-(4-hydroxy-phenyl)-1,1-dimethyl-ethylamino]-ethyl}-4H-benzo[1, 4]oxazin-3-one
- 6-hydroxy-8-{1-hydroxy-2-[2-(4-isopropyl-phenyl)-1.1dimethyl-ethylamino]-ethyl}-4H-benzo[1, 4]oxazin-3-one
- 8-{2-[2-(4-ethyl-phenyl)-1,1-dimethyl-ethylamino]-1-hydroxy-ethyl}-6-hydroxy-4H-benzo[1, 4]oxazin-3-one
- 8-{2-[2-(4-ethoxy-phenyl)-1,1-dimethyl-ethylamino]-1-hydroxy-ethyl}-6-hydroxy-4H-benzo[1, 4]oxazin-3-one
- 4-(4-{2-[2-hydroxy-2-(6-hydroxy-3-oxo-3.4-dihydro-2H-benzo[1,4]oxazin-8-yl)-ethylamino]-2-methyl-propyl}-phenoxy)-butyric acid
- 8-{2-[2-(3.4-difluoro-phenyl)-1,1-dimethyl-ethylamino]-1-hydroxy-ethyl}-6-hydroxy-4H-benzo[1,4]oxazin-3-one
- 1-(4-ethoxy-carbonylamino-3-cyano-5-fluorophenyl)-2-(tert-butylamino)ethanol
- 2-hydroxy-5-(1-hydroxy-2-{2-[4-(2-hydroxy-2-phenyl-ethylamino)-phenyl]-ethylamino}-ethyl)-benzaldehyde
- N-[2-hydroxy-5-(1-hydroxy-2-{2-[4-(2-hydroxy-2-phenyl-ethylamino)-phenyl]-ethylamino}-ethyl)-phenyl]-formamide
- 8-hydroxy-5-(1-hydroxy-2-{2-[4-(6-methoxy-biphenyl-3-ylamino)-phenyl]-ethylamino}-ethyl)-1H -quinolin-2-one
- 8-hydroxy-5-[1-hydroxy-2-(6-phenethylamino-hexylamino)-ethyl]-1H-quinolin-2-one
- 5-[2-(2-{4-[4-(2-amino-2-methyl-propoxy)-phenylamino]-phenyl}-ethylamino)-1-hydroxy-ethyl]-8-hydroxy-1H-quinolin-2-one
- [3-(4-{6-[2-hydroxy-2-(4-hydroxy-3-hydroxymethyl-phenyl)-ethylamino]-hexyloxy}-butyl)-5-methyl-phenyl]-urea
- 4-(2-{6-[2-(2.6-dichloro-benzyloxy)-ethoxy]-hexylamino}-1-hydroxy-ethyl)-2-hydroxymethyl-phenol
- 3-(4-{6-[2-hydroxy-2-(4-hydroxy-3-hydroxymethyl-phenyl)-ethylamino]-hexyloxy}-butyl)-benzylsulphonamide
- 3-(3-{7-[2-hydroxy-2-(4-hydroxy-3-hydroxymethyl-phenyl)-ethylamino]-heptyloxy}-propyl)-benzylsulphonamide
- 4-(2-{6-[4-(3-cyclopentanesulphonyl-phenyl)-butoxy]-hexylamino}-1-hydroxy-ethyl)-2-hydroxymethyl-phenol
- N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

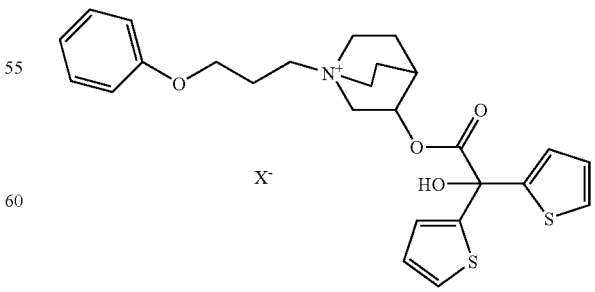

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

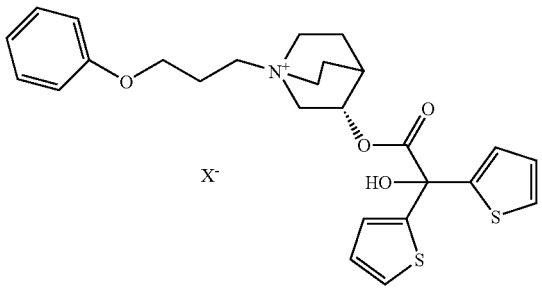

AC-1-en wherein X⁻ may have the above-mentioned meanings. Other preferred anticholinergics are selected from the salts of formula AC-2

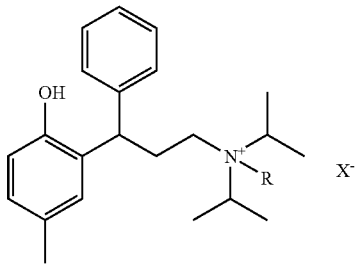

AC-2 wherein R denotes either methyl or ethyl and wherein X⁻ may have the above-mentioned meanings. In an alternativen embodiment the compound of formula AC-2 may also be present in the form of the free base AC-2-base.

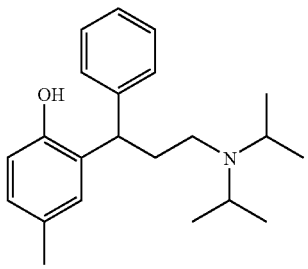

AC-2-base

Other specified compounds are:
tropenol 2,2-diphenylpropionate methobromide;
scopine 2,2-diphenylpropionate methobromide;
scopine 2-fluoro-2,2-diphenylacetate methobromide;
tropenol 2-fluoro-2,2-diphenylacetate methobromide;
tropenol 3,3',4,4'-tetrafluorobenzilate methobromide;
scopine 3,3',4,4'-tetrafluorobenzilate methobromide;
tropenol 4,4'-difluorobenzilate methobromide;
scopine 4,4'-difluorobenzilate methobromide;
tropenol 3,3'-difluorobenzilate methobromide;
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tertamethylcyclo-propylcarbonyl)oxy-androstra-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and

- N-(3,5-dichloro-1-oxo-pyridin-4-yl)-4-difluoromethoxy-3-cyclopropylmethoxybenzamide
- (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
- (R)-(+)-1-(4-bromobenzyl)-4-[(3-cyclopentyloxy)-4-methoxyphenyl]-2-pyrrolidone
- 3-(cyclopentyloxy-4-methoxyphenyl)-1-(4-N'-[N-2-cyano-S-methyl-isothioureido]benzyl)-2-pyrrolidone
- cis[4-cyano-4-(3-cyclopentyloxy-4-methoxyphenyl)cyclohexane-1-carboxylic acid]
- 2-carbomethoxy-4-cyano-4-(3-cyclopropylmethoxy-4-difluoromethoxy-phenyl)cyclohexan-1-one
- cis[4-cyano-4-(3-cyclopropylmethoxy-4-difluoromethoxyphenyl)cyclohexan-1-ol]
- (R)-(+)-ethyl[4-(3-cyclopentyloxy-4-methoxyphenyl)pyrrolidin-2-ylidene]acetate
- (S)-(−)-ethyl[4-(3-cyclopentyloxy-4-methoxyphenyl)pyrrolidin-2-ylidene]acetate
- 9-cyclopentyl-5,6-dihydro-7-ethyl-3-(2-thienyl)-9H-pyrazolo[3,4-c]-1,2,4-triazolo[4,3-a]pyridine
- 9-cyclopentyl-5,6-dihydro-7-ethyl-3-(tert-butyl)-9H-pyrazolo[3,4-c]-1,2,4-triazolo[4. 3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the PDE4 inhibitors are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and

- 1-(((R)-(3-(2-(6,7-difluoro-2-quinolinyl)ethenyl)phenyl)-3-(2-(2-hydroxy-2-propyl)phenyl)thio)methylcyclopropane-acetic acid,
- 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methylcyclopropaneacetic acid
- [2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention these acid addition salts are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and

- 4-[(3-chloro-4-fluorophenyl)amino]-6-{[4-(morpholin-4-yl)-1-oxo-2-buten-1-yl]amino}-7-cyclopropylmethoxy-quinazoline
- 4-[(3-chloro-4-fluorophenyl)amino]-6-{[4-(N,N-diethylamino)-1-oxo-2-buten-1-yl]amino}-7-cyclopropylmethoxy-quinazoline
- 4-[(3-chloro-4-fluorophenyl)amino]-6-{[4-(N,N-dimethylamino)-1-oxo-2-buten-1-yl]amino}-7-cyclopropylmethoxy-quinazoline
- 4-[(R)-(1-phenyl-ethyl)amino]-6-{[4-(morpholin-4-yl)-1-oxo-2-buten-1-yl]amino}-7-cyclopentyloxy-quinazoline
- 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline
- 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline
- 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline
- 4-[(3-chloro-4-fluoro-phenyl)amino]-6-[2-((S)-6-methyl-2-oxo-morpholin-4-yl)-ethoxy]-7-methoxy-quinazoline
- 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline
- 4-[(3-chloro-4-fluorophenyl)amino]-6-{[4-(N,N-dimethylamino)-1-oxo-2-buten-1-yl]amino}-7-cyclopentyloxy-quinazoline
- 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline
- 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline
- 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline
- 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline
- 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline
- 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline
- 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline
- 4-[(3-chloro-4-fluorophenyl)amino]-6-{[4-(N-cyclopropyl-N-methyl-amino)-1-oxo-2-buten-1-yl]amino}-7-cyclopentyloxy-quinazoline
- 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-bis-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxyacetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline
4-[(3-chloro-4-fluoro-phenyl)amino]-6-[trans-4-(N-methanesulphonyl-N-methyl-amino)-cyclohexan-1-yloxy]-7-methoxy-quinazoline
4-[(3-chloro-4-fluoro-phenyl)amino]-6-(trans-4-dimethylamino-cyclohexan-1-yloxy)-7-methoxy-quinazoline
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline
4-[(3-chloro-4-fluoro-phenyl)amino]-6-(1-methanesulphonyl-piperidin-4-yloxy)-7-methoxy-quinazoline
4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention these acid addition salts are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

It is also possible to use inhalable macromolecules, as disclosed in EP 1 003 478.

In addition, the compounds may come from the groups of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

For inhalation, suitable substances include pharmaceutical compositions containing the above-mentioned active substances, as well as the salts and esters thereof and combinations of these active substances, salts and esters.

Preferably the housing is non-releasably connected to the mouthpiece. If the housing is glued or welded to the mouthpiece, for example, the user of the inhaler cannot gain access to the drug without destroying the inhaler.

The housing expediently comprises an air intake opening for inhaling powdered medicaments. When the patient breathes in or inhales through the mouthpiece the air entering the interior through the air intake opening becomes charged with the medicament.

According to one feature a component for dispersing particles is associated with the mouthpiece. The component ensures a fine, inhalable distribution of medicament. The component is conveniently formed in one piece with the mouthpiece or an inhalation channel of the inner cavity. The component may be produced for example by injection moulding together with the mouthpiece made of plastics or the inhalation channel of the housing, which is also made of plastics. According to a further feature the component is constructed as a screen or the like.

Preferably the plastics are polymers, thermoplastic polycondensates, polyadducts, modified natural substances or rubbers or mixtures of these plastics.

Particularly preferred are polyolefins, vinyl chloride polymers, styrene polymers, polyacetals, polyamides, thermoplastic polyesters and polyarylethers or mixtures of these plastics. Examples of these plastics are polyethylene, polyvinyl chloride, polyoxymethylene, polyacetal, acrylonitrile/butadiene/styrene (ABS), acrylonitrile/styrene/acrylic ester (ASA), polyamides, polycarbonate, poly(ethyleneterephthalate), poly(butyleneterephthalate) or poly(phenylene ether). Plastics of this kind may be obtained for example from the company Ensinger in Nufringen, Germany.

In order to dispense with additional packaging of the drug, it is expediently contained in the inner cavity. According to another embodiment the medicament is contained in a capsule inserted in the inner cavity. The capsule for holding the medicament has proved valuable in that it provides additional protection from environmental influences. To improve the operation the inhaler still further, the inner cavity is filled by the manufacturer with the medicament or the capsule containing the medicament.

Preferably at least one pin is provided for piercing the capsule. In particular, two pins are provided, one pin being associated with a region of the capsule facing the mouthpiece, while the other pin is associated with an opposing region.

According to a further feature the pin is coupled to an actuating element which is mounted on a capsule chamber of the inhaler such that when it is actuated the pin is driven into the capsule and/or the pin is withdrawn from the capsule. The actuating element that causes the pin to pierce the capsule on actuation is particularly easy to operate if the capsule is only to be opened immediately before using the inhaler. The actuating element may be adapted to be operated either by pressing, pulling or displacement. To assist the withdrawal of the pin from the capsule, the actuating element is spring-loaded relative to the capsule chamber.

Expediently, the pin has already pierced the capsule in the inhaler as supplied. If the pin is already in the capsule in the inhaler as supplied, the pin is withdrawn from the capsule by actuation of the actuating element, either by pressing or pulling. This procedure is advantageous in that by the application of relatively little force on the part of the user of the inhaler, it is ensured that the pins have made a hole of a predetermined size in the capsule and hence the delivery rate of the medicament for inhalation is guaranteed. Moreover, the pins projecting into the capsule secure the capsule in a predetermined position in the inner cavity of the housing, i.e. in a capsule chamber.

Preferably the pin is made of plastics. As the inhaler is used only once and so is the pin, it is not absolutely necessary for the pin to be made of stainless steel. Of course, it is also possible to use a known pin made of metal, particularly stainless steel. The skilled man will choose the appropriate material and will determine its geometry depending on the requirements imposed on the pin.

Alternatively the capsule is removably arranged with two spaced-apart openings on corresponding holders in the capsule chamber. Thus, it is not necessary to fit movable pins. Rather, the user of the inhaler can release the capsule from the holders which are formed as posts, for example, by an abrupt movement of the inhaler, for example.

In order that the inhaler is ready for use without any further action on the part of the user, the capsule is preferably fixed on the holders in such a way that it is freed by an air current caused by inhaling and thus releases the substance.

For visual inspection the capsule chamber is made of a transparent material. As the capsule chamber is not surrounded by other components, the user can see immediately whether, for example, all the medicament contained therein has been inhaled.

For protecting the medicament for inhalation and the inhaler from environmental influences, the inhaler is provided with airtight outer packaging, particularly a foil container. Outer packaging of this kind is conventional. Alternatively or additionally the mouthpiece and/or the air intake opening may be tightly sealed by a removable cap. As a result of these measures the inner cavity of the inhaler containing the medicament is protected from, in particular, influences that will damage the medicament, such as moisture, for example, with minimal packaging costs.

It will be appreciated that the features described above and those yet to be explained hereinafter may be used not only in the particular combinations specified but also in other combinations. The scope of the invention is defined only by the claims.

The invention will hereinafter be described in more detail using a number of embodiments by way of example, with reference to the accompanying drawings.

The inhaler according to FIG. 1 consists essentially of a housing 1 comprising an inner cavity for receiving an inhalable medicament, which comprises on the one hand a mouthpiece 2 and on the other hand an air intake opening 3. A screen 5 for dispersing particles of the medicament to be inhaled is arranged in an inhalation channel 4 at the end with the mouthpiece 2. A capsule 7 containing powdered medicament and to be opened by two spaced-apart pins 8 movably mounted in the housing 1 is inserted in a capsule chamber 6 in the inner cavity of the housing 1. For removing the pins 8 from the capsule 7 a compression spring 9 is provided which is supported partly on the housing 1 and partly on an actuating element 10 connected to the pins 8. The capsule 7 is placed in the capsule chamber 6 of the housing 1 by the manufacturer and the housing 1 is then fixedly connected to the in this case tubular mouthpiece 2, after which it is impossible to remove the capsule 7.

A user of the inhaler removes it from its airtight packaging, which protects the medicament particularly from environmental influences, and then acts on the actuating element 10 to drive the two pins 8 into the capsule 7. After the actuating element 10 has been released it returns to its original position under the effect of the compression spring 9. The user places the mouthpiece 2 in his mouth for inhalation and sucks air into the housing 1 through the air inlet opening 3 in the direction of the arrow 11, thus causing the capsule 7 to vibrate, as a result of which the medicament is expelled and passes through the mouthpiece 2 in the direction of the arrow 12 into the user's airway. After inhalation the user can dispose of the inhaler as it is intended for single use only.

Figure 2:
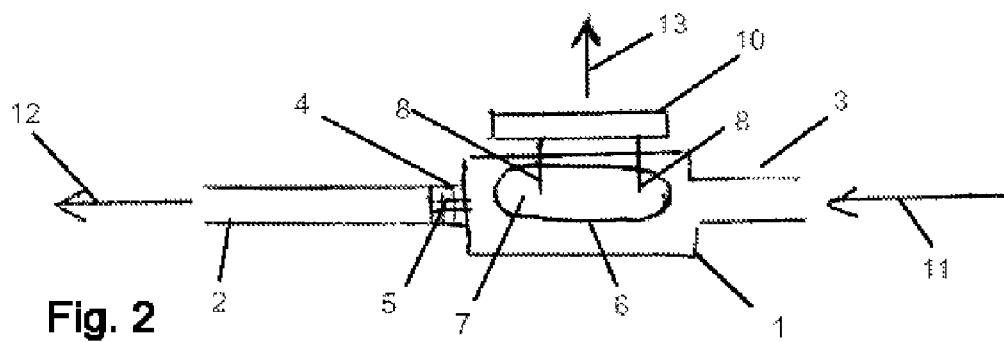
FIG. 2 is a schematic view of the inhaler according to FIG. 1 in an alternative embodiment and FIG. 3 is a schematic view of the inhaler according to FIG. 1 in another alternative embodiment.

According to FIG. 2 the pins 8 have already been driven into the capsule 7 by the manufacturer and therefore in order to use the inhaler they have to be withdrawn from the capsule 7 in the direction of the arrow 13 by means of the actuating element 10, in order to free the openings in the capsule 7 to allow the medicament to be expelled. Consequently, there is no need for the patient to pierce the capsule 7 and the diameter of the pins 8 may be adapted to the required delivery rate of the inhalable powder without having to take account of the force needed to drive the pins 7 into the capsule 7 made of plastics, for example. The pins 7 driven into the capsule 7 seal the capsule by virtue of the elastic resilience of the material from which the capsule is made, thus ensuring that the powdered medicament cannot escape from the capsule 7, and they secure the capsule 7 in the capsule chamber 6.

Figure 3:
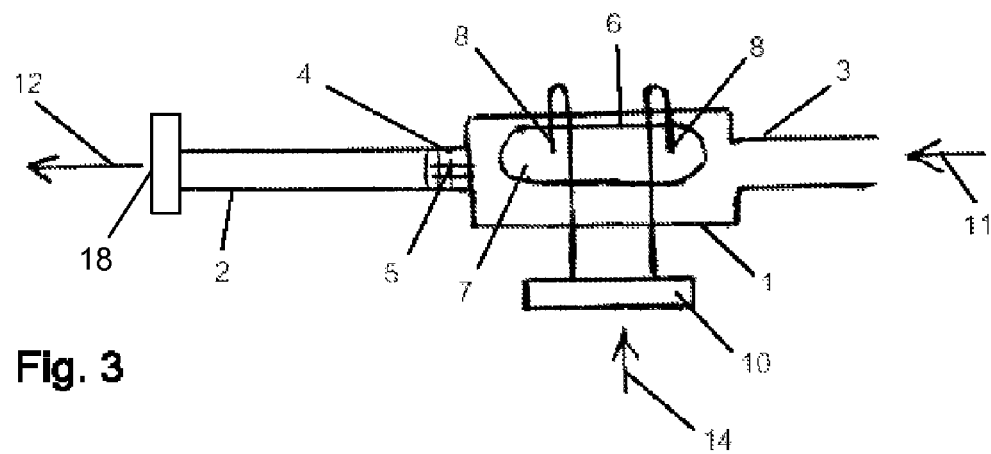

In the inhaler according to FIG. 3 the pins 8 have again already been driven into the capsule 7 by the manufacturer. The actuating element 10 is mounted on the housing 1 such that in order to remove the pins 8 from the capsule 7 to free the openings in the capsule 7 it has to be operated by pressing in the direction of the arrow 14. The mouthpiece 2 and/or the air intake opening may be tightly sealed by a removable cap 18.

What is claimed is:

1. An inhaler for administering a medicament in the form of inhalable substances, formulations, or mixtures of substances, comprising:
    a housing comprising an inner cavity adapted to hold the medicament,
    a mouth piece wherein the housing is rigidly connected to the mouthpiece such that the inner cavity is coupled to a mouthpiece,
    a capsule including the medicament comprised within the housing,
    at least one piercing means driven into the capsule, and
    at least one actuating element mounted on the inhaler in a manner that an initial actuation of the actuating element causes the piercing means to pull out of the capsule.

2. The inhaler according to claim 1, wherein the housing is non-releasably coupled to the mouthpiece.

3. The inhaler according to claim 1, wherein the housing has an air intake opening for the inhalation of powdered medicaments.

4. The inhaler according to claim 1, wherein a component for dispersing particles is associated with the mouthpiece.

5. The inhaler according to claim 4, wherein the component is formed in one piece with the mouthpiece or an inhalation channel of the inner cavity.

6. The inhaler according to claim 4, wherein the component is constructed as a screen.

7. The inhaler according to claim 1, wherein the inner cavity is filled by the manufacturer with the capsule containing the medicament.

8. The inhaler according to claim 1, wherein the at least one piercing means is a pin is provided for piercing the capsule.

9. The inhaler according to claim 1, wherein the actuating element is spring-loaded relative to the capsule chamber.

10. The inhaler according to claim 1, wherein the capsule is releasably arranged with two spaced-apart openings on corresponding holders in the capsule chamber.

11. The inhaler according to claim 10, wherein the capsule is secured on the holders in such a way that it is freed by an air current produced by inhalation and releases the medicament.

12. The inhaler according to claim 1, wherein the inner cavity comprises a transparent material.

13. The inhaler according to claim 1, wherein the mouthpiece or the air intake opening is closed off by a removable cap.

14. The inhaler according to claim 1, wherein it is for single use.

15. The inhaler according to claim 1 for administering a powdered medicament.

16. The inhaler according to claim 1 for administering a powdered medicament containing an active substance selected from among the anticholinergics, betamimetics, steroids, phosphodiesterase IV-inhibitors, LTD4-antagonists, EGFR-kinase inhibitors, antiallergics, ergot alkaloid derivatives, triptanes, CGRP-antagonists, phosphodiesterase-V-inhibitors, and combinations of active substances of these kinds.

17. The inhaler of claim 8, wherein a diameter of the pin is configured based on a required delivery rate of the medicament.

18. The inhaler of claim 1, wherein the at least one piercing means seals the capsule to prevent escape of the medicament from the capsule.

* * * * *